US012593761B2

(12) United States Patent
Spiess et al.

(10) Patent No.: US 12,593,761 B2
(45) Date of Patent: Apr. 7, 2026

(54) COMPOSITIONS AND METHODS FOR POLLEN STORAGE

(71) Applicant: Monsanto Technology LLC, St. Louis, MO (US)

(72) Inventors: Gretchen Spiess, St. Louis, MO (US); Chad A. Stendal, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/678,685

(22) Filed: Feb. 23, 2022

(65) Prior Publication Data

US 2022/0279739 A1      Sep. 8, 2022

Related U.S. Application Data

(60) Provisional application No. 63/155,714, filed on Mar. 2, 2021.

(51) Int. Cl.
| | |
|---|---|
| *A01G 24/15* | (2018.01) |
| *A01H 1/02* | (2006.01) |
| *A01N 3/02* | (2006.01) |

(52) U.S. Cl.
CPC ............. *A01G 24/15* (2018.02); *A01H 1/027* (2021.01); *A01N 3/02* (2013.01)

(58) Field of Classification Search
CPC ........... A01G 24/15; A01N 3/02; A01H 1/027
See application file for complete search history.

(56) References Cited

U.S. PATENT DOCUMENTS

| | | |
|---|---|---|
| 10,575,517 B2 | 3/2020 | Cope et al. |
| 11,344,027 B2 | 5/2022 | Cope et al. |
| 2014/0289909 A1 | 9/2014 | Byrum et al. |

| | | |
|---|---|---|
| 2019/0008144 A1 | 1/2019 | Etter et al. |
| 2019/0380289 A1 | 12/2019 | Cope et al. |
| 2021/0307273 A1 | 10/2021 | Boyer et al. |

FOREIGN PATENT DOCUMENTS

| | | | | |
|---|---|---|---|---|
| CN | 107371862 | | 11/2017 | |
| CN | 107371862 A | * | 11/2017 | ......... A01G 13/0212 |
| CN | 107494522 | | 12/2017 | |
| CN | 108781981 | | 11/2018 | |
| CN | 108781981 A | * | 11/2018 | ............ A01G 17/00 |
| GB | 2425954 A | * | 11/2006 | ............ A01N 25/00 |

OTHER PUBLICATIONS https://en.wikipedia.org/wiki/Perlite; Dec. 2, 2022; 6 pages.*
Franchi et al.; Anther opening, pollen biology and stigma receptivity in the long blooming species, *Pareitaria judaica* L. (Urticaceae); 2007; 10 pages.*
Pfahler, et al. In vitro germination and pollen tube growth of maize (*Zea mays* L.) pollen. Planta 111, 253-259 (1973).
Rauf, et al. Breeding Strategies to Enhance Drought Tolerance in Crops. In: Al-Khayri, J., Jain, S., Johnson, D. (eds) Advances in Plant Breeding Strategies: Agronomic, Abiotic and Biotic Stress Traits. Springer, Cham. (2016).
Sartoris. Longevity of Sugarcane and Corn Pollen—A Method for Long-Distance Shipment of Sugarcane Pollen by Airplane. Am J Bot, pp. 395-400, 1942.
International Search Report and Written Opinion regarding International App. No. PCT/US2022/07506, mailed May 18, 2022.

* cited by examiner

*Primary Examiner* — Kent L Bell
(74) *Attorney, Agent, or Firm* — Dentons US LLP; Christopher Luzecky

(57) ABSTRACT

The invention provides novel compositions and methods for storage and delivery of pollen to a female reproductive part of a recipient plant. The pollen storage composition provided includes at least one perlite particle and pollen. The methods provided include storing the pollen storage composition and applying the pollen storage composition to at least a first female reproductive part of a recipient plant, thereby pollinating the female reproductive part with the pollen from the donor plant.

6 Claims, No Drawings

COMPOSITIONS AND METHODS FOR POLLEN STORAGE

REFERENCE TO RELATED APPLICATION

This application claims the benefit of U.S. Provisional Application No. 63/155,714, filed Mar. 2, 2021, which is herein incorporated by reference in its entirety.

FIELD OF THE INVENTION

The present disclosure relates to the field of agricultural biotechnology, and more specifically to compositions and methods for short term pollen storage.

BACKGROUND OF THE INVENTION

Pollen viability is significantly influenced by environmental conditions and may decrease rapidly once it is shed from the plant. Pollen from the Poaceae family of plants, which includes many economically important crops such as corn, rice, and wheat, remains viable for a particularly short time after it is shed. Methods to improve pollen viability and fertilization potential following pollen storage are of significant value to the agricultural industry.

SUMMARY

In one aspect, a pollen storage composition is provided herein comprising: (a) at least one perlite particle; and (b) pollen. In some embodiments, the at least one perlite particle is present in the composition at a vol:vol ratio of about 0.1:1 to about 9:1 relative to the pollen. In specific embodiments, the at least one perlite particle is present in the composition at a vol:vol ratio of about 1:1 to about 2:1 relative to the pollen. In some embodiments the at least one perlite particle may comprise expanded perlite or raw perlite. In one embodiment, the pollen is pollen from a monocot plant. In certain embodiments, the at least one perlite particle comprises from about 70% to about 80% silicon dioxide by weight or from about 10% to about 15% aluminum oxide by weight. In one embodiment, the at least one perlite particle comprises from about 70% to about 80% silicon dioxide and from about 10% to about 15% aluminum oxide by weight. In another embodiment, the at least one perlite particles comprises from about 2% to about 6% sodium oxide by weight. In yet another embodiment, the pollen storage composition comprises a plurality of perlite particles having a mean diameter of from about 30 μm to about 600 μm, from about 30 μm to about 350 μm, or from about 30 μm to about 150 μm. In one embodiment, a pollen storage composition provided herein is defined as free or substantially free of an added liquid, for example, water or another liquid. In further embodiments, such a composition may be defined as a dry or substantially dry pollen storage composition.

In another aspect, a method for storing pollen comprising storing pollen in the presence of at least one perlite particle is provided herein. In certain embodiments, the storing is performed at about 0.5° C. to about 10° C. or at about 90% to about 100% relative humidity. In some embodiments, the storing is performed for up to about 14 days or for from about 1 day to about 7 days. In one embodiment, the pollen is pollen from a monocot plant. In another embodiment, the pollen is capable of germination following the storing. In certain embodiments, the at least one perlite particle and the pollen are comprised in a pollen storage composition described herein. The pollen storage composition may comprise, for example, a vol:vol ratio of perlite to pollen of about 0.1:1 to about 9:1 or of about 1:1 to about 2:1, expanded perlite, raw perlite, from about 70% to about 80% silicon dioxide by weight, from about 10% to about 15% aluminum oxide by weight, from about 2% to about 6% sodium oxide by weight, or a plurality of perlite particles having a mean diameter of from about 30 μm to about 600 μm, from about 30 μm to about 350 μm, or from about 30 μm to about 150 μm.

In yet another aspect, a method for delivery of pollen to a female reproductive part of a recipient plant is provided herein, the method comprising the steps of: (a) obtaining a pollen storage composition comprising at least one perlite particle and pollen from a donor plant; and (b) delivering said storage composition to at least a first female reproductive part of the recipient plant, thereby pollinating the female reproductive part with the pollen from the donor plant. In one embodiment, the pollen storage composition is stored according to the methods of storing pollen described herein prior to delivering the storage composition to at least a first female reproductive part of the recipient plant. The pollen storage composition may be stored, for example, for up to about 14 days, from about 1 day to about 7 days, at about 0.5° C. to about 10° C., or at about 90% to about 100% relative humidity prior to delivering the storage composition to at least a first female reproductive part of the recipient plant. In one embodiment, the plant is a corn plant. In another embodiment, the method produces a substantially equivalent number of seeds compared to the number of seeds produced with pollination using pollen that was not stored. In yet another embodiment, the method further comprises collecting seed resulting from the pollinating, or repeating said steps (a) and (b) on two or more consecutive days. In one embodiment, the method further comprises crossing a progeny plant grown from a seed resulting from the pollinating with itself or a second plant. In another embodiment, the delivering comprises hand or mechanical application of pollen. In yet another embodiment, the pollen storage composition is delivered as a composition that is free or substantially free of an added liquid, for example, water or another liquid. In still yet another embodiment, the pollen storage composition is delivered as a pollen storage composition that is defined as dry or substantially dry. In one embodiment, the pollen storage composition is mixed with a liquid prior to delivering the pollen storage composition to a recipient plant. In another embodiment, the pollen storage composition is delivered as a liquid pollen suspension solution.

DETAILED DESCRIPTION

Modern plant breeding relies on outcrossing or cross-pollination to generate progeny plants having specific heritable traits. Such breeding strategies play an important role in $F_1$ population development and trait integration. Corn (*Zea mays*), rice (*Oryza sativa*), and wheat (*Triticum aestivum*), which belong to the Poaceae family and the Liliopsida class (monocots) of plants, are examples of economically important agricultural crops in which breeding has been hampered by low efficiency procedures in controlled cross-pollination. Conventional methods for cross pollination of such species, for example corn, entails emasculation of female plants and interspersing rows of male parent plants. This process is inefficient as it depends on the effective flow of pollen to the female plants, which is vulnerable to wind and requires that the male and female plants enter the reproductive phase at the same time.

Storage of pollen in manner that maintains viability and fertilization potential would allow for pollination that does not depend on active pollen shed, temporal synchrony with female flower receptivity, or the use of male sterility. Pollen viability often decreases rapidly once it is shed from the plant, and pollen from the Poaceae family of plants, such as corn (*Zea mays*), rice (*Oryza sativa*), and wheat (*Triticum aestivum*), remains viable for a particularly short time period. Therefore, improved methods to maintain pollen viability and fertilization potential during storage are needed and are of significant value to the agricultural industry.

Pollen viability is significantly influenced by environmental conditions, such as temperature and humidity. In fact, it is well settled that storage under high humidity, low temperature conditions significantly increases pollen viability (Sartoris, *Am J Bot*, pp. 395-400, 1942). Furthermore, storage at low temperature (e.g., 2° C.) can significantly increase pollen viability even when relative humidity is not controlled (Pfahler and Linskens, *Planta*, 111(3): 253-259, 1973).

The invention represents a significant advance in the art in that it permits successful mechanical application of stored pollen. Application of stored pollen at the scale required for field seed production has previously been unfeasible. The current invention, however, surprisingly overcomes limitations in the art by permitting cross-pollination using stored pollen, eliminating the need for in-field synchronized male and female plant development, and minimizing the effects of variable weather conditions. Furthermore, the pollen storage compositions and methods provided herein allow for the production of full seed set. Therefore, the pollen storage compositions and methods of the present invention can be used to mechanically distribute stored pollen to entire fields.

The present disclosure therefore permits implementation of high-throughput methods for the delivery of stored donor pollen to a recipient female reproductive part of a plant. The methods provided herein substantially reduce the time and labor previously required to facilitate cross-pollination in plants. This is of particular significance as modern plant breeding programs may require thousands or even millions of individual crosses on a yearly basis in order to produce a new plant variety with improved traits.

Pollen Storage Compositions

In one aspect, the present invention provides a pollen storage composition comprising at least one perlite particle and pollen. As used herein, "pollen" refers to at least one pollen grain and may comprise a plurality of pollen grains. The term "about" is used to indicate that a value includes the standard deviation of the mean for the device or method being employed to determine the value. Non-limiting examples of pollen that may be used according to the compositions and methods of the invention include pollen collected from a dicot plant, a monocot plant, a Poaceae family plant, a corn plant, a rice plant, or a wheat plant. As used herein "perlite" refers to an composition comprising silicon dioxide and aluminum oxide. Perlite may be mined as an amorphous volcanic glass or may be produced synthetically. Raw perlite may be expanded by heating to a temperature which causes the water molecules trapped inside to turn to vapor. Raw perlite may be expanded for example by heating to a temperature of about 850° C. to about 900° C. In a one example, raw perlite may be expanded by heating to a temperature greater than about 870° C. Non-limiting examples of perlite include Harborlite® 200, Harborlite® 500, Harborlite® 600, Harborlite® 635, Harborlite® 700, Harborlite® 700S, Harborlite® 800, Harborlite® 800S, Harborlite® 900, Harborlite® 900S, Harborlite® 1500, Harborlite® 1500S, Harborlite® 1800, Harborlite® 1800S, Harborlite® 1900, Harborlite® 1950S, Harborlite® 2000, Harborlite® 2000S, Harborlite® 2100S, Dicalite® HP100, Dicalite® HP110, Dicalite® HP120, Dicalite® HP125, Dicalite® HP200, Dicalite® HP210, Dicalite® HP220, Dicalite® HP225, Dicalite® HP900, and Dicalite® HP910, Dicalite® HP920, Dicalite® HP925, Dicalite® HP1500, Dicalite® HP1510, Dicalite® HP1520, Dicalite® HP1525, Dicalite® HP2000, Dicalite® HP2010, Dicalite® HP2020, Dicalite® HP2025, Dicalite® HP2035, Dicalite® HP2300, Dicalite® HP2310, Dicalite® HP2320, Dicalite® HP2325, Dicalite® HP2335. In some embodiments, the components for use in the pollen storage composition may be optimized for a particular application. Such parameters can be determined empirically using the methodology described herein. In general, it will be desirable to use a composition containing components that maintain pollen viability and fertilization potential and facilitate uniform pollen dispersal. As used herein a "vol:vol ratio" refers to the volume:volume ratio of two substances. When these two substances are, for example, at least one perlite particle and pollen, the ratio is calculated by comparing the volume of the at least one perlite particle to the volume of the pollen. As a non-limiting example the volume of the at least one perlite particle and pollen may be measured in $mm^3$, $cm^3$, or $m^3$. In some embodiments, the at least one perlite particle is present in the composition at a vol:vol ratio of about 0.1:1 to about 9:1 relative to the pollen. In specific embodiments, the at least one perlite particle is present in the composition at a vol:vol ratio of about 1:1 to about 2:1 relative to the pollen. The at least one perlite particle may be present, for example, in the composition at a vol:vol ratio of about 0.1:1, 0.2:1, 0.3:1, 0.4:1, 0.5:1, 0.6:1, 0.7:1, 0.8:1, 0.9:1; 1:1, 1:1, 2:1, 2:1, 3:1, 4:1, 5:1, 5:1, 6:1, 7:1 8:1 or 9:1 relative to the pollen, including all ranges derivable therebetween. In some embodiments the at least one perlite particle may comprise expanded perlite or raw perlite. In some embodiments the at least one perlite particle comprises from about 70% to about 80% silicon dioxide by weight or from about 10% to about 15% aluminum oxide by weight. The at least one perlite particle may comprise, for example, about 70%, 71%, 72%, 73%, 74%, 75%, 76%, 77%, 78%, 79%, or 80% silicon dioxide by weight or about 10%, 11%, 12%, 13%, 14%, or 15% aluminum oxide by weight, including all ranges derivable therebetween. In one embodiment, the at least one perlite particles comprises from about 2% to about 6% sodium oxide by weight. The at least one perlite particle may comprise, for example, about 2%, 3%, 4%, 5% or 6% sodium oxide by weight, including all ranges derivable therebetween. The at least one perlite particle may additionally comprise potassium oxide, iron oxide, calcium oxide, or sulfur oxide. The at least one perlite particle may comprise, for example, about 0% to about 9% potassium oxide, about 0% to about 3% sulfur oxide, about 0% to about 5% iron oxide, or about 0% to about 5% calcium oxide by weight. The at least one perlite particle may comprise, for example, about 0%, 1%, 2%, 3%, 4%, 5%, 6%, 7%, 8%, or 9% potassium oxide, about 0%, 0.5%, 1%, 1.5%, 2%, 2.5% or 3% sulfur oxide, about 0%, 0.5%, 1.0%, 1.5%, 2%, 2.5%, 3%, 3.5%, 4%, 4.5%, or 5.0% iron oxide, or about 0%, 0.5%, 1%, 1.5%, 2%, 2.5%, 3%, 3.5%, 4%, 4.5%, or 5% calcium oxide by weight, including all ranges derivable therebetween. In another embodiment, the pollen storage composition comprises a plurality of perlite particles having a mean diameter of from about 30 μm to about 600 μm, from about 30 μm to about 350 μm, or from about 30 μm to about 150 μm. The plurality of perlite particles may for example have a mean diameter of about 30 μm, about 40 μm, about 50 μm, about 60 μm, about 70 μm, about 80 μm, about 90 μm, about 100 μm, about 120 μm, about 140 μm, about 160 μm, about 160 μm, about 180 μm, about 200 μm, about 220 μm, about 240 μm, about 260 μm, about 280 μm, about 300 μm, about 330 μm, about 350 μm, about 400 μm, about 450 μm, about 500 μm, about 550 μm, or about 600 μm, including all ranges derivable therebetween. Non-limiting examples of such perlite particles include Harborlite® 1500S, Dicalite® HP100, Dicalite® HP120, Dicalite® HP200, Dicalite® HP220, and Dicalite® HP900. Harborlite® 1500S has a median particle size of about 37.6 μm and comprises about 76.8% silicon dioxide, 12.8% aluminum oxide, 5.3% potassium oxide, 3.7% sodium oxide, 0.6% iron oxide, and 0.5% calcium oxide. Dicalite® HP100 has a median particle size of about 300-330 μm and comprises about 70-80% silicon dioxide, 10-15% aluminum oxide, 2-6% sodium oxide, 0-3% potassium oxide, 0-3% sulfur oxide, and 0-5% other trace inorganic minerals. Dicalite® HP120 has a median particle size of about 300-330 μm, is coated with siloxane, and comprises about 70-80% silicon dioxide, 10-15% aluminum oxide, 2-6% sodium oxide, 0-3% potassium oxide, 0-3% sulfur oxide, and 0-5% other trace inorganic minerals. Dicalite® HP200 has a median particle size of about 110-125 μm and comprises about 70-80% silicon dioxide, 10-15% aluminum oxide, 2-6% sodium oxide, 0-3% potassium oxide, 0-3% sulfur oxide, and 0-5% other trace inorganic minerals. Dicalite® HP220 has a median particle size of about 110-125 μm, is coated with siloxane, and comprises about 70-80% silicon dioxide, 10-15% aluminum oxide, 2-6% sodium oxide, 0-3% potassium oxide, 0-3% sulfur oxide, and 0-5% other trace inorganic minerals. Dicalite® HP900 has a medium particle size of about 80-90 μm and comprises about 70-80% silicon dioxide, 10-15% aluminum oxide, 2-6% sodium oxide, 0-3% potassium oxide, 0-3% sulfur oxide, and 0-5% other trace inorganic materials. In one embodiment, a pollen storage composition provided herein is defined as free or substantially free of an added liquid, for example, water or another liquid. In further embodiments, such a composition may be defined as a dry or substantially dry pollen storage composition.

Storing Plant Pollen

In another aspect, the invention provides a method of storing pollen comprising storing pollen in the presence of at least one perlite particle. In some embodiments, the conditions of the storage method may be optimized for a particular application or particular pollen type. Such parameters can be determined empirically using the methodology described herein. To promote cross-pollination, for example, it may be desired to use a pollen storage compositions and methods that contain components that facilitate uniform pollen dispersal, maintain high viability of the pollen grains, and which do not significantly hinder fertilization and seed development when applied to the female reproductive part of a recipient plant. Non-limiting examples of pollen that may be used according to the compositions and methods of the invention include pollen collected from a dicot plant, a monocot plant, a Poaceae family plant, a corn plant, a rice plant, or a wheat plant.

In certain embodiments, storing may performed at about 0.5° C. to about 10° C. or at about 90% to about 100% relative humidity. The storing may be performed, for example, at about 0.5° C., 1° C., 2° C., 3° C., 4° C., 5° C., 6° C., 7° C., 8° C., 9° C., or 10° C., or at about 90%, 91%, 92%, 93%, 94%, 95%, 96%, 97%, 98%, 99%, or 100% relative humidity, including all ranges derivable therebetween. In one embodiment, the pollen may be stored in humidity chamber. In another embodiment, the airflow rate in the humidity chamber is between about 5.0 liters/min (l/min) and about 20.0 l/min. The airflow rate, for example, may be about 5.0 l/min, 6.0 l/min, 7.0 l/min, 8.0l/min, 9.0 l/min, 10.0 l/min, 11.0 l/min, 12.0 l/min, 13.0 l/min, 14.0 l/min, 15.0 l/min, 16.0 l/min, 17.0 l/min, 18.0 l/min, 19.0 l/min, or 20.0 l/min, including all ranges derivable therebetween. In another embodiment, the airflow rate is an airflow rate which is sufficient to maintain a humidity chamber at about 0.5° C. to about 10° C. and/or at about 90% to about 100% relative humidity. An airflow rate of about 5.0 l/min to about 20.0 l/min for example is sufficient to maintain the humidity chamber at about 0.5° C. to about 10° C. and at about 90% to about 100% relative humidity for pollen volumes ranging from 1 grain to about 45 liters, however, the airflow rate required may be greater as the volume of pollen increases. The airflow rate required to maintain a humidity chamber at about 0.5° C. to about 10° C. and about 90% to about 100% relative humidity for any pollen volume may be determined empirically using the methods described herein, and potentially any airflow rate could find use in accordance with the invention. In some embodiments, the storing is performed for up to about 14 days or for from about 1 day to about 7 days. The storing may be performed, for example, for about 1 second, 15 seconds, 30 seconds, 45 seconds, 1 minute, 5 minutes, 15 minutes, 30 minutes, 45 minutes, 1 hour, 2 hours, 4 hours, 6 hours, 8 hours, 10 hours, 12 hours, 14 hours, 16 hours, 18 hours, 20 hours, 22 hours, 1 day, 2 days, 3 days, 4 days, 5 days, 6 days, 7 days, 8 days, 9 days, 10 days, 11 days, 12 days, 13 days, or 14 days, including all ranges derivable therebetween. In one embodiment, the pollen is pollen from a monocot plant. In another embodiment, the pollen is capable of germination following storing. In certain embodiments, the at least one perlite particle and the pollen are comprised in a pollen storage composition as described herein. The pollen storage composition may comprise, for example, a vol:vol ratio of perlite to pollen of about 0.1:1 to about 9:1, a vol:vol ratio of perlite to pollen of about 1:1 to about 2:1, expanded perlite, raw perlite, from about 70% to about 80% silicon dioxide by weight, from about 10% to about 15% aluminum oxide by weight, from about 2% to about 6% sodium oxide by weight, or a plurality of perlite particles having a mean diameter of from about 30 μm to about 600 μm, from about 30 μm to about 350 μm, or from about 30 μm to about 150 μm.

Delivery of Stored Pollen for Pollination of Plants

The present invention surprisingly permits cross-pollination of potentially any flowering plant or grass using stored pollen. The methods provided herein include obtaining a pollen storage composition comprising at least one perlite particle and pollen from a donor plant, and delivering the storage composition to at least a first female reproductive part of the recipient plant, thereby pollinating the female reproductive part with the pollen from the donor plant. In one embodiment, the pollen storage composition is delivered as a composition that is free or substantially free of an added liquid, for example, water or another liquid. In another embodiment, the pollen storage composition is delivered as a composition that is defined as dry or substantially dry. In yet another embodiment, the pollen storage composition is mixed with a liquid prior to delivering the pollen storage composition to a recipient plant. In still yet another embodiment, the pollen storage composition is delivered as a liquid pollen suspension solution. In some embodiments, the methods of the invention may be optimized for a particular application, particular plant species, or particular pollen type. Such parameters can be determined empirically using the methodology described herein. Non-limiting examples of plants that may be used according to the methods of the invention include dicot plants, monocot plants, Poaceae family plants, corn plants, rice plants, and wheat plants. In some embodiments, the delivering comprises hand or mechanical application of pollen. As used herein, the term "hand application" refers to manually transferring pollen to the female reproductive part of a recipient plant. Non-limiting examples of hand application include applying pollen with a cotton swab or small brush and using a measuring spoon to transfer pollen from a container, such as a bag or graduated tube, to the female reproductive part of a recipient plant. As used herein "mechanical application" refers to application of pollen using a mechanical device. Non-limiting examples of such a mechanical device include an air-assisted pollen applicator or a pollen applicator with a common agricultural nozzle. In certain embodiment the agricultural nozzle may be rated for "fine" or "very fine" sprays. In one embodiment, mechanical application may be performed, for example, using a pollen applicator with an exit air velocity of about 1 m/s to about 10 m/s, including all ranges derivable therebetween. In another embodiment, the pollen storage composition may be applied at a pressure of about 10 psi, about 15 psi, about 20 psi, about 25 psi, about 30 psi, about 35 psi, or about 40 psi. In still yet another embodiment, air-assisted spraying is used to produce a pollen storage composition spray having a volume weighted mean droplet diameter between about 30 μm to about 600 μm, between about 30 μm and about 350 μm, or between about 30 μm and about 150 μm. The pollen storage composition spray may have a volume weighted mean droplet diameter, for example, of about 30 μm, about 40 μm, about 50 μm, about 60 μm, about 70 μm, about 80 μm, about 90 μm, about 100 μm, about 120 μm, about 140 μm, about 160 μm, about 160 μm, about 180 μm, about 200 μm, about 220 μm, about 240 μm, about 260 μm, about 280 μm, about 300 μm, about 330 μm, about 350 μm, about 400 μm, about 450 μm, about 500 μm, about 550 μm, or about 600 μm, including all ranges derivable therebetween. Air-assisted spraying is also described in U.S. Provisional App. Ser. No. 63/005,260, which is incorporated herein by reference.

In certain embodiments, the pollen storage composition is stored according to the methods described herein prior to delivering the storage composition to at least a first female reproductive part of the recipient plant. The pollen storage composition may be stored, for example, for up to about 14 days, from about 1 day to about 7 days, at about 0.5° C. to about 10° C., or at about 90% to about 100% relative humidity prior to delivering the storage composition to at least a first female reproductive part of the recipient plant.

To promote cross-pollination, it may be desired to use a pollen storage composition containing components that facilitate uniform pollen dispersal, maintain high viability of the pollen grains, and which do not significantly hinder fertilization and seed development when applied to the female reproductive part of a recipient plant. Examples of such components include, but are not limited to, Harborlite® 1500S, Dicalite® HP100, Dicalite® HP120, Dicalite® HP200, Dicalite® HP220, and Dicalite® HP900.

In particular embodiments, the methods described herein may comprise repeating the steps of obtaining a pollen storage composition comprising at least one perlite particle and pollen from a donor plant and delivering the storage composition to at least a first female reproductive part of the recipient plant on two or more consecutive days. These steps may be repeated, for example, on two consecutive days, three consecutive days, four consecutive days, or on five or more consecutive days. In corn, for example, it can be found that repeating the delivering steps on two or three consecutive days can result in higher seed set.

In still other embodiments, the methods described herein may comprise pollination of flowers that are male sterile at the time of pollinating. Depending upon the developmental stage of the plant, donor pollen applied for cross-pollination could compete with pollen produced by the recipient plant. In order to improve the efficacy of the cross-pollination, it may be advantageous in some cases that the recipient plant be male sterile in an effort to reduce competition with selfing. Thus, a male sterility system could be employed with the female parent plant in a particular cross. Many such male sterility systems are well known, including cytoplasmic male sterility (CMS) and genic male sterility (GMS). CMS and GMS facilitate hybrid seed production for many crops and thus allow breeders to harness yield gains associated with hybrid vigor. The use of a gametocide presents an alternative method to produce male sterility. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of Roundup® herbicide in combination with glyphosate tolerant corn plants to produce male sterile corn plants is disclosed in PCT Publication WO 98/44140. Several gametocides have been reported effective in inducing pollen sterility in various crops and are well known in the art. Such gametocides include sodium methyl arsenate, 2,3-dichloroisobutyrate, sodium 2,2-dichloropropionate, gibberellic acid, maleic hydrazide (1,2-dihydro-pyridazine, 3-6-dione), 2,4-dichloro phenoxy acetic acid, ethyl 4-fluorooxanilate, trihalogenated methylsulfonamides, ethyl and methyl arsenates (Ali et al., 1999). Physical emasculation of the recipient plant presents another alternative to produce male sterility. Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because the male reproductive portion, and thereby pollen bearing parts, have been previously removed from all plants of the plant being used as the female in the hybridization. Of course, during this hybridization procedure, the parental varieties are grown such that they are isolated from other plants to minimize or prevent any accidental contamination of pollen from foreign sources. These isolation techniques are well within the ability of those skilled in this art.

In particular embodiments, the methods described herein are carried out to produce a substantially equivalent number of seeds compared to the number of seeds produced using pollen that has not been stored. Substantial equivalence is evaluated by comparing seed sets produced using stored pollen to seed sets produced using pollen that was not stored. As used herein, "substantially equivalent" refers to a characteristic wherein the mean value±standard deviation of the test population does not deviate more than about 20% from the mean value±standard deviation of the control population. In corn, it was found that at least the following pollen storage compositions produce a substantially equivalent number of seeds compared to the number of seeds produced using a pollen that was not stored: Harborlite® 1500S and Dicalite® HP900 (Table 12).

The step of collecting seed resulting from pollinating with a pollen storage composition of the invention may also be carried out. In a particular embodiment, a progeny plant produced from the collected seed may be crossed with itself or a different plant. In certain embodiments, a method of producing hybrid seed is provided herein comprising producing a pollen storage composition of the invention, delivering the pollen storage composition onto a female reproductive part of a recipient plant, thereby pollinating the female reproductive part with the pollen from the donor plant, harvesting seed produced from the pollination; and identifying hybrid progeny. Selecting a progeny seed or plant that results from pollinating with the pollen storage composition may also performed. Identifying and selecting progeny could be facilitated by use of a polymorphic marker allele contained in the pollen donor that serves to identify progeny plants or seeds of that donor. Morphological markers or biochemical/protein markers have commonly been used as tools for selection of plants with desired traits in breeding. Molecular marker techniques that have been extensively used and are particularly promising for application to plant breeding include: restriction fragment length polymorphisms (RFLPs), amplified fragment length polymorphisms (AFLPs), random amplified polymorphic DNA (RAPD), microsatellites or simple sequence repeats (SSRs), and single nucleotide polymorphisms (SNPs) (Al-Khayri et al., 2016).

The methods disclosed herein may be implemented for improved cross-pollination of potentially any plants. Such plants can include, but are not limited to, members of the Poaceae family, non-limiting examples of which are corn, wheat, and rice.

Modified Plants and Seeds

One aspect of the invention provides selection of progeny plants and seeds that result from the methods described herein. In some embodiments, the progeny plants and seeds may be defined as comprising a detectable modification relative to the female parent plant. One method of producing such plants and seeds is through use of an allele produced by plant genetic transformation. Suitable methods for transformation of host plant cells for use with the current invention are well known in the art and include any method by which DNA can be introduced into a cell (for example, where a recombinant DNA construct is stably integrated into a plant chromosome) and are well known in the art. Some widely utilized methods for cell transformation are *Agrobacterium*-mediated transformation, microprojectile bombardment-mediated transformation, and cell penetrating peptide-mediated delivery of DNA modifying agents.

Another method of producing modified plants and seeds is through genome editing. As used herein, the term "genome editing" refers to the use of genome editing methods and a site-specific genome modification enzyme to modify a nucleotide sequence. In some embodiments, donor pollen may be transformed using techniques known in the art to contain one or more reagents that mediate genome-specific modification in a plant. Pollen grains may be used in accordance with the invention that comprise any such reagents of loci generated with use of such reagents at any current or prior generation.

Suitable methods for altering a wild-type DNA sequence at a pre-determined chromosomal site include any method known in the art. Targeted modification of plant genomes through the use of genome editing methods and reagents can be used to create improved plant lines through modification of plant genomic DNA. In addition, genome editing methods and reagents can facilitate targeted insertion of one or more nucleic acids of interest into a plant genome. Exemplary methods for introducing donor polynucleotides into a plant genome or modifying the genomic DNA of a plant include the use of genome editing reagents such as: sequence-specific recombinases, endonucleases, zinc-finger nucleases, engineered or native meganucleases, TALE-endonucleases, RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system), and CRISPR-associated transposases (Strecker, et al., 2019) and (Klompe, et al. 2019). Several embodiments relate to methods of genome editing using single-stranded oligonucleotides to introduce precise base pair modifications in a plant genome, as described by Sauer et al. (*Plant Physiol.* 170(4): 1917-1928; 2016).

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break or a double-strand break. In some embodiments, a site-specific genome modification enzyme comprises a cytidine deaminase or an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

EXAMPLES

Example 1. Development of Pollen Storage Compositions

Pollen grains may be obtained from a donor plant and stored as a pollen storage composition prior to pollination of a recipient plant. The components and concentrations in the pollen storage composition are important to the efficacy of the composition, as they influence not only the pollen viability but also the success rate of hybrid seed production in pollinated plants. While efficiency can be improved by optimization of the components and concentrations in a given pollen storage composition, numerous substitutions and modifications are possible while still achieving pollination. Table 1 includes results produced using different methods of pollen application conducted on different days with distinct female recipient plants. The results provided in Table 1 are, however, representative of the potential for certain pollen storage compositions to produce relatively high seed set compared to other pollen storage compositions, which were relatively unsuccessful. The results in Table 1, are further representative of the potential for certain pollen storage compositions to produce relatively high seed set compared to pollen stored in the absence of a pollen storage composition.

TABLE 1

| Exemplary pollen storage compositions and representative number of kernels produced following 3-7 days of pollen storage prior to pollen application. | |
| --- | --- |
| Pollen Storage Composition (ratios given as additive:pollen; vol:vol) | No. Kernels Produced |
| Pollen Only (Fresh) | 307.7 ± 5.5 |
| Pollen Only (Stored, 5 days) | 84.7 ± 63.5 |
| Perkasil ® SM 660 ® SM 660 (1:1) | 108.7 ± 13.5 |
| Dicalite ® HP100 (2:1) | 125.8 ± 29.9 |
| Dicalite ® HP120 (2:1) | 90.8 ± 28.8 |
| Dicalite ® HP200 (2:1) | 129.7 ± 26.7 |
| Dicalite ® HP200 (3:1) | 179.0 ± 45.7 |
| Dicalite ® HP220 (2:1) | 186.4 ± 36.5 |
| Dicalite ® HP900 (2:1) | 259.3 ± 50.7 |
| Dicalite ® HP900 (3:1) | 254.3 ± 51.4 |
| Harborlite ® 1500S (2:1) | 267.7 ± 21.4 |
| Harborlite ® 1500S (1:1) | 104.0 ± 13.0 |
| Harborlite ® 1500S (1:2) | 22.3 ± 7.3 |

Tests were performed to develop pollen storage compositions that maintain high pollen viability and produce seed when applied to the female reproductive part of a recipient plant. A number of additives were tested for use in the pollen storage composition, including Perkasil® SM 660, Dicalite® HP100, Dicalite® HP120, Dicalite® HP200, Dicalite® HP220, Dicalite® HP900, and Harborlite® 1500S. The Harborlite® line of products is manufactured by Imerys®. The Dicalite® line of products is manufactured by Dicaperl®. Stored pollen storage compositions comprising Dicalite® HP900 and Harborlite® 1500S produced seed sets comparable to those produced using fresh pollen (Table 1).

Based on the results obtained from experiments testing individual pollen storage compositions, it was determined that beneficial components for a pollen storage composition include, but are not limited to, the following: Perkasil® SM 660, Dicalite® HP100, Dicalite® HP120, Dicalite® HP200, Dicalite® HP220, Dicalite® HP900, and Harborlite® 1500S, all of which produce increased seed sets compared to pollen stored without additive.

In certain embodiments, solutions and methods described herein may be used together with any plant. In specific embodiments, compositions and methods provided may be used together with crop plants, such as monocot crop plants. Non-limiting examples of crop plants that may be used together with the compositions and methods described herein include corn, wheat, barley, rice, sorghum, and soybean.

Example 2. Analysis of Seed Set Following Hand Pollination Using Stored Corn Pollen Achieving full seed set using stored pollen is challenging. Pollen viability can be lost in minutes to hours depending on species and environmental conditions. Exposure to dry air and high temperature is particularly detrimental. Furthermore, many additives which preserve pollen viability react negatively with corn silks and thus result in reduced seed sets. Pollen storage compositions and methods were developed to overcome these challenges to produce full seed sets using stored pollen.

Suitable pollen storage compositions were evaluated by examining seed set following hand pollination with pollen stored using one of the following pollen storage compositions (ratios are provided as vol:vol additive:pollen): 1) fresh corn pollen (M08); 2) corn pollen (M08) stored in Perkasil® SM 660 (1:1); 3) corn pollen (M08) stored in Harborlite®

1500S (2:1); 4) corn pollen (M08) stored in Harborlite® 1500S (1:1); or 5) corn pollen (M08) stored in Harborlite® 1500S (1:2). Pollen storage compositions were stored in a humidity chamber at 3.8° C. and 97% humidity with an airflow of 8.0 l/min for 7 days prior to hand pollination. 32 mg of pollen was used for each pollination and seed set was evaluated 10 days post pollination. Pollinations for each pollen storage composition were performed in triplicate. Pollen storage compositions comprising Harborlite® 1500S (2:1) produced a high seed set following hand pollination (Table 2).

TABLE 2

| Seed set following hand pollination using M08 corn pollen stored for 7 days. | | | | |
| --- | --- | --- | --- | --- |
| Composition | Ear 1 | Ear 2 | Ear 3 | Average |
| Fresh pollen | 156 | 403 | N/A | 279.5 ± 123.5 |
| Perkasil ® SM 660 (1:1) | 119 | 82 | 125 | 108.7 ± 13.5 |
| Harborlite ® 1500S (2:1) | 246 | 214 | 135 | 198.3 ± 33.0 |
| Harborlite ® 1500S (1:1) | 103 | 127 | 82 | 104.0 ± 13 |
| Harborlite ® 1500S (1:2) | 36 | 11 | 20 | 22.3 ± 7.3 |

Suitable pollen storage compositions were evaluated by examining seed set following hand pollination with pollen stored using one of the following pollen storage compositions (ratios are provided as vol:vol additive:pollen): 1) fresh pollen (M02); 2) stored corn pollen (M02); 3) corn pollen (M02) stored in Perkasil® SM 660 (1:1); or 4) corn pollen (M02) stored in Harborlite® 1500S (2:1). Pollen storage compositions were stored in a humidity chamber at 3.8° C. and 97% humidity with an airflow of 8.0 l/min for 5 days prior to hand pollination. 32 mg of pollen was used for each pollination, and pollinations for each pollen storage composition were performed in triplicate. Six replicate pollinations were performed using fresh M02 pollen. The pollinations using fresh M02 pollen produced 300, 384, 265, 188, 243, and 223 kernels per ear, respectively. Pollen germination was evaluated on storage day 3 and storage day 5 (Table 3). Fresh M02 pollen had an average germination of 62.9±01.0% on day 0. Seed set was evaluated 13 days post pollination. Pollen storage compositions comprising Harborlite® 1500S (2:1) produced a high seed set following hand pollination (Table 4).

TABLE 3

| Germination of M02 corn pollen stored in compositions comprising Perkasil ® SM 660 or Harborlite ® 1500S. | | |
| --- | --- | --- |
| Composition | Avg. % Germ Day 3 | Avg. % Germ. Day 5 |
| Perkasil ® SM 660 (1:1) | 37.2 ± 6.4 | 7.5 ± 2.5 |
| Harborlite ® 1500S (2:1) | 37.1 ± 1.8 | 17.6 ± 2.1 |

TABLE 4

| Seed set following hand pollination using M02 corn pollen stored for 5 days in compositions comprising Perkasil ® SM 660 or Harborlite ® 1500S. | | | | |
| --- | --- | --- | --- | --- |
| Composition | Ear 1 | Ear 2 | Ear 3 | Average |
| Fresh pollen | | | | 267.2 ± 68.6 |
| Stored pollen | 10 | 4 | 8 | 7.3 ± 3.1 |
| Perkasil ® SM 660 (1:1) | 163 | 193 | 199 | 185.0 ± 19.3 |
| Harborlite ® 1500S (2:1) | 325 | 322 | 344 | 330.3 ± 11.9 |

Suitable pollen storage compositions were evaluated by examining seed set following hand pollination with pollen stored using one of the following pollen storage compositions (ratios are provided as vol:vol additive:pollen): 1) fresh corn pollen (M02); 2) stored corn pollen (M02); 3) corn pollen (M02) stored in Harborlite® 1500S (2:1); 4) corn pollen (M02) stored in Dicalite® HP200 (2:1); 5) corn pollen (M02) stored in Dicalite® HP200 (3:1); 6) corn pollen (M02) stored in Dicalite® HP900 (2:1); or 7) corn pollen (M02) stored in Dicalite® HP900 (3:1). Pollen storage compositions were stored in a humidity chamber at 4.0° C. and 96.5% humidity with an airflow of 20.0 l/min for 5 days prior to hand pollination. 32 mg of pollen was used for each pollination. Pollinations for each pollen storage composition were performed in triplicate. Pollen germination was evaluated on storage day 5 (Table 5). Seed set was evaluated 15 days post pollination. Pollen storage compositions comprising Dicalite® HP900 showed a high seed set following hand pollination (Table 6).

TABLE 5

Germination of M02 corn pollen stored in compositions comprising Harborlite ® 1500S, Dicalite ® HP200, or Dicalite ® HP900.

| Composition | Avg. % Germ. Day 5 |
| --- | --- |
| Fresh pollen | 73.1 ± 0.4 |
| Stored pollen | 33.5 ± 2.6 |
| Harborlite ® 1500S (2:1) | 37.9 ± 1.4 |
| Dicalite ® HP200 (2:1) | 41.6 ± 0.4 |
| Dicalite ® HP200 (3:1) | 26.7 ± 1.4 |
| Dicalite ® HP900 (2:1) | 30.0 ± 4.4 |
| Dicalite ® HP900 (3:1) | 23.7 ± 5.8 |

TABLE 6

Seed set following hand pollination using M02 corn pollen stored for 5 days in compositions comprising Harborlite ® 1500S, Dicalite ® HP200, or Dicalite ® HP900.

| Composition | Ear 1 | Ear 2 | Ear 3 | Average |
| --- | --- | --- | --- | --- |
| Fresh pollen | 298 | 308 | 317 | 307.7 ± 5.5 |
| Stored pollen | 4 | 40 | 210 | 84.7 ± 63.5 |
| Harborlite ® 1500S (2:1) | 235 | 172 | 73 | 160.0 ± 47.2 |
| Dicalite ® HP200 (2:1) | 81 | 135 | 173 | 129.7 ± 26.7 |
| Dicalite ® HP200 (3:1) | 126 | 270 | 141 | 179.0 ± 45.7 |
| Dicalite ® HP900 (2:1) | 308 | 312 | 158 | 259.3 ± 50.7 |
| Dicalite ® HP900 (3:1) | 199 | 207 | 357 | 254.3 ± 51.4 |

Suitable pollen storage compositions were evaluated by examining seed set following hand pollination with pollen stored using one of the following pollen storage compositions (ratios are provided as vol:vol additive:pollen): 1) fresh corn pollen (M08); 2) stored corn pollen (M06 and M08); 3) corn pollen (M06 and M08) stored in Harborlite® 1500S (2:1); or 4) corn pollen (M06 and M08) stored in Dicalite® HP900 (2:1). Pollen storage compositions were stored in a humidity chamber at 4.0° C. and 96.5% humidity with an airflow of 20.0 l/min for 7 days prior to hand pollination. 32 mg of pollen was used for each pollination, and pollinations for each pollen storage composition were performed in quadruplicate. Pollen germination was evaluated on storage day 7 (Table 7). Seed set was evaluated 13 days post pollination. Pollen storage compositions comprising Harborlite® 1500S and Dicalite® HP900 produced a high seed set following hand pollination (Table 8).

TABLE 7

Germination of M06 and M08 corn pollen stored in compositions comprising Harborlite ® 1500S or Dicalite ® HP900.

| Composition | Avg. % Germ. Day 7 |
| --- | --- |
| Fresh pollen (M08) | 69.8 ± 4.6 |
| Stored pollen (M08) | 27.7 ± 10.4 |
| Harborlite ® 1500S (M08) | 20.7 ± 6.6 |
| Dicalite ® HP900 (M08) | 25.9 ± 3.2 |
| Stored pollen (M06) | 22.0 ± 2.4 |
| Harborlite ® 1500S (M06) | 4.8 ± 3.3 |
| Dicalite ® HP900 (M06) | 8.0 ± 3.3 |

TABLE 8

Seed set following hand pollination using M08 and M06 corn pollen stored for 7 days in compositions comprising Harborlite ® 1500S or Dicalite ® HP900.

| Composition | Ear 1 | Ear 2 | Ear 3 | Ear 4 | Average |
| --- | --- | --- | --- | --- | --- |
| Fresh pollen (M08) | 348 | 363 | 296 | 379 | 346.5 ± 36.0 |
| Stored pollen (M08) | 239 | 313 | 265 | 215 | 258.0 ± 42.0 |
| Harborlite ® 1500S (M08) | 247 | 290 | 295 | 250 | 270.5 ± 25.5 |
| Dicalite ® HP900 (M08) | 381 | 308 | 269 | 326 | 321.0 ± 46.5 |
| Stored pollen (M06) | 225 | 299 | 249 | 252 | 256.3 ± 31.0 |
| Harborlite ® 1500S (M06) | 84 | 158 | 63 | 135 | 110.0 ± 44.0 |
| Dicalite ® HP900 (M06) | 233 | 270 | 284 | 239 | 256.5 ± 24.5 |

Example 3. Analysis of Seed Set Following Mechanical Pollination Using Stored Corn Pollen Suitable pollen storage compositions were evaluated by examining seed set following mechanical or hand pollination with pollen stored using one of the following pollen storage compositions (ratios are provided as vol:vol additive:pollen): 1) fresh corn pollen (M08); 2) corn pollen (M08) stored in Harborlite® 1500S (2:1), hand pollination; or 3) corn pollen (M08) stored in Harborlite® 1500S (2:1), mechanical pollination. Pollen storage compositions were stored in a humidity chamber at 4° C. and 97% humidity for 5-7 days prior to hand or mechanical pollination. Mechanical pollination was performed using an applicator test stand with agitation and an exit air velocity of 2.13 m/s. 32 mg of pollen was used for each pollination. Mechanical pollination was performed on three consecutive days corresponding to storage days 5, 6, and 7. Pollen germination was evaluated on storage days 5, 6, and 7 both prior to and after mechanical application. Fresh M08 corn pollen had an average germination of 64.7±1.4% on day 0. Mechanical pollination had no effect on pollen germination rates (Table 9). Seed set was evaluated 19 days after the first pollen application. Pollen storage compositions comprising Harborlite® 1500S produced a similar seed set following mechanical pollination compared to hand pollination (Table 10).

TABLE 9

Germination of M08 corn pollen stored in Harborlite ® 1500S before and after mechanical application.

| Storage Day | Avg. % Germ (pre-application) | Avg. % Germ. (post-application) |
| --- | --- | --- |
| 5 | 22.8 ± 1.9 | 24.3 ± 4.4 |
| 6 | 10.6 ± 2.4 | 13.0 ± 0.9 |
| 7 | 8.3 ± 1.2 | 6.0 ± 0.8 |

TABLE 10

Seed set following hand or mechanical pollination using M08 corn pollen stored in Harborlite ® 1500S.

| Composition | Ear 1 | Ear 2 | Ear 3 | Average |
|---|---|---|---|---|
| Harborlite ® 1500S, hand pollination | 202 | N/A | N/A | 202 |
| Harborlite ® 1500S, mechanical pollination | 230 | 269 | 304 | 267.7 ± 21.4 |

Suitable pollen storage compositions were evaluated by examining seed set following mechanical pollination with pollen stored using one of the following pollen storage compositions (ratios are provided as vol:vol additive:pollen): 1) fresh or stored corn pollen (M08); 2) corn pollen (M08) stored in Harborlite® 1500S (2:1); 3) corn pollen (M08) stored in Dicalite® HP100 (2:1); 4) corn pollen (M08) stored in Dicalite® HP120 (2:1); 5) corn pollen (M08) stored in Dicalite® HP200 (2:1); 6) corn pollen (M08) stored in Dicalite® HP220 (2:1); 7) corn pollen compositions comprising Harborlite® 1500S, Dicalite® HP200, Dicalite® HP220, and Dicalite® HP900 produced a high seed set following storage for 3 days and mechanical pollination. (Table 12).

TABLE 11

Germination of M08 corn pollen stored in Harborlite ® 1500S, Dicalite ® HP100, Dicalite ® HP120, Dicalite ® HP200, Dicalite ® HP220, or Dicalite ® HP900.

| Composition | Avg. % Germ. Day 3 |
|---|---|
| Pollen only | 80.5 ± 1.1 |
| Harborlite ® 1500S | 73.0 ± 1.5 |
| Dicalite ® HP100 | 61.0 ± 0.5 |
| Dicalite ® HP120 | 53.7 ± 8.5 |
| Dicalite ® HP200 | 63.5 ± 0.7 |
| Dicalite ® HP220 | 58.8 ± 1.6 |
| Dicalite ® HP900 | 68.4 ± 4.3 |
| Pollen only, desiccant chamber | 58.3 ± 0.6 |
| Harborlite ® 1500S, desiccant chamber | 60.3 ± 2.9 |

TABLE 12

Seed set following mechanical pollination using M08 corn pollen stored in Harborlite ® 1500S, Dicalite ® HP100, Dicalite ®, HP120, Dicalite ® HP200, Dicalite ® HP220, or Dicalite ® HP900.

| Composition | Ear 1 | Ear 2 | Ear 3 | Ear 4 | Ear 5 | Average |
|---|---|---|---|---|---|---|
| Fresh pollen, storage day 0 | 285 | 330 | 261 | 233 | N/A | 277.3 ± 41.1 |
| Harborlite ® 1500S, storage day 0 | 315 | 276 | 228 | 210 | N/A | 257.3 ± 47.5 |
| Dicalite ® HP100, storage day 0 | 159 | 275 | 168 | 259 | N/A | 215.3 ± 60.2 |
| Dicalite ® HP120, storage day 0 | 319 | 296 | 267 | 280 | N/A | 290.5 ± 22.4 |
| Dicalite ® HP200, storage day 0 | 278 | 256 | 234 | 251 | N/A | 280.0 ± 50.8 |
| Dicalite ® HP220, storage day 0 | 283 | 274 | 328 | 312 | N/A | 299.3 ± 25.1 |
| Dicalite ® HP900, storage day 0 | 287 | 309 | 357 | 275 | N/A | 307.0 ± 36.2 |
| Stored pollen, storage day 3 | 217 | 139 | 135 | 102 | 121 | 142.8 ± 43.9 |
| Harborlite ® 1500S, storage day 3 | 270 | 201 | 135 | 250 | 312 | 233.6 ± 68.1 |
| Dicalite ® HP100, storage day 3 | 154 | 142 | 86 | 102 | 145 | 125.8 ± 29.9 |
| Dicalite ® HP120, storage day 3 | 65 | 140 | 78 | 87 | 84 | 90.8 ± 28.8 |
| Dicalite ® HP200, storage day 3 | 180 | 176 | 176 | 234 | 189 | 191.0 ± 24.6 |
| Dicalite ® HP220, storage day 3 | 213 | 174 | 147 | 235 | 163 | 186.4 ± 36.5 |
| Dicalite ® HP900, storage day 3 | 266 | 276 | 184 | 272 | 265 | 252.6 ± 38.6 |
| Pollen only, desiccant chamber 1.5 hr, storage day 3 | 154 | 160 | 244 | 159 | 63 | 156.0 ± 64.1 |
| Harborlite ® 1500S, desiccant chamber 1.5 hr, storage day 3 | 149 | 160 | 112 | 215 | 257 | 178.6.0 ± 57.3 |

(M08) stored in Dicalite® HP900 (2:1); 8) stored corn pollen (M08), placed in desiccant chamber at 4° C. 1.5 hour prior to application; 9) corn pollen (M08) stored in Harborlite® 1500S (2:1) and placed in desiccant chamber at 4° C. 1.5 hours to application. Pollen storage compositions were stored in a humidity chamber at 4° C. and 97% humidity with an airflow of 8.0 l/min for 3 days prior to mechanical pollination. Of note, numerous experiments have shown that using an airflow between about 5.0 l/min and about 20.0 l/min produces the same results. Mechanical pollination was performed using an applicator test stand with agitation and exit air velocity of 2.13 m/s. 32 mg of pollen was used for each pollination. Mechanical pollination was performed on three consecutive days with either fresh pollen or pollen stored for 3 days. Four or five replicate mechanical pollinations were performed for each pollen storage composition. Pollen germination was evaluated on storage day 3 (Table 11). Fresh M08 corn pollen had an average germination of 88.6±1.5% on day 0. Seed set was evaluated 17 days after the first pollen application. Nine replicate hand pollinations (3 per day) were performed as a positive control. Hand pollination produced 282.0±73.8 kernels/ear. Pollen storage

What is claimed is:

1. A composition formulated for storing pollen, comprising:

(a) at least one perlite particle; and (b) pollen;

wherein the at least one perlite particle is present in the composition at a volume:volume ratio of 1:1 to about 5:1 relative to said pollen;

wherein the composition is designed to maintain the viability and fertilization potential of the pollen.

2. The composition of claim 1, wherein the at least one perlite particle:

a) comprises expanded perlite;

b) comprises raw perlite;

c) comprises from about 70% to about 80% silicon dioxide by weight;

d) comprises from about 10% to about 15% aluminum oxide by weight; or e) comprises from about 70% to about 80% silicon dioxide and from about 10% to about 15% aluminum oxide by weight.

3. The composition of claim 1, wherein the at least one perlite particle is present in the composition at a vol:vol ratio of about 1:1 to about 2:1 relative to said pollen.

4. The composition of claim 1, wherein the pollen is pollen from a monocot plant.

5. The composition of claim 2, wherein the at least one perlite particle further comprises from about 2% to about 6% sodium oxide by weight.

6. The composition of claim 1, wherein the composition comprises a plurality of perlite particles having a mean diameter of from about 30 $\mu$m to about 600 $\mu$m.

\* \* \* \* \*